United States Patent [19]

Fisher et al.

[11] 4,046,753

[45] Sept. 6, 1977

[54] SUBSTITUTED 2-PHENYLHYDRAZINO AND 2-PHENYLAZO THIAZOLINES

[75] Inventors: Michael H. Fisher, Somerville; Mu Tsu Wu, Clark, both of N.J.

[73] Assignee: Merck & Co., Inc., Rahway, N.J.

[21] Appl. No.: 619,000

[22] Filed: Oct. 2, 1975

Related U.S. Application Data

[63] Continuation of Ser. No. 405,714, Oct. 11, 1973, abandoned.

[51] Int. Cl.$^2$ .............. C07C 107/04; C07D 277/04; C07D 277/08; C07D 277/38
[52] U.S. Cl. ............................. 260/158; 260/306.7 R; 260/306.7 T; 260/306.8 R; 260/552 SC; 424/14; 424/226; 424/270; 426/532; 426/540
[58] Field of Search .............. 260/306.7 R, 306.8 R, 260/158, 306.7 T

[56] References Cited

U.S. PATENT DOCUMENTS

| | | | |
|---|---|---|---|
| 3,311,614 | 3/1967 | Capps | 260/239.3 |
| 3,328,416 | 6/1967 | Wilhelm et al. | 260/307.6 T |
| 3,468,899 | 9/1969 | Barber et al. | 260/306.8 R |
| 3,651,053 | 3/1972 | Sagner et al. | 260/243 R |

FOREIGN PATENT DOCUMENTS

| | | | |
|---|---|---|---|
| 1,458,956 | 10/1966 | France | 260/306.7 R |
| 42-3310 | 2/1967 | Japan | 260/158 |

OTHER PUBLICATIONS

Beilstein (I), "Handbuch der Organischen Chemie", vol. 27, pp. 148 and 452, (1937).
Beilstein (II), "Handbuch der Organischen Chemie", vol. 27, 2nd supplement, pp. 194 and 495, (1955).
CIBA (II), Chemical Abstracts, vol. 64, 15892a (1966).
Sommer et al., Index Chemicus, vol. 31, No. 103328 (1968).
KAI, Index Chemicus, vol. 33, No. 111325 (1969).
Theilheimer (I), Synthetic Methods of Organic Chemistry, vol. 6, p. 232, No. 646 (1952).
Theiheimer (II), "Synthetic Methods of Organic Chemistry", vol. 12, p. 297, No. 674 (1958).
Houben-Weyl (I), Methoden der Organischen Chemie, vol. X/2, pp. 321 to 322 (1967).
Elderfield, "Heterocyclic Compounds", vol. 5, pp. 595 to 596 (1956).
Houben-Weyl (II), Methoden der Organischen Chemie, vol. X/31, pp. 377 to 380 (1965).

Primary Examiner—Floyd D. Higel
Attorney, Agent, or Firm—David L. Rose; J. Jerome Behan

[57] ABSTRACT

Thiazolines substituted at the 2-position with 2-substituted phenylhydrazino or 2-substituted phenylazo groups are disclosed. The hydrazino group may also be substituted. The compounds are active anthelmintics, antihypertensive and ectoparasiticidal agents.

7 Claims, No Drawings

SUBSTITUTED 2-PHENYLHYDRAZINO AND 2-PHENYLAZO THIAZOLINES

This application is a continuation of application Ser. No. 405,714, filed Oct. 11, 1973, now abandoned.

SUMMARY OF THE INVENTION

This invention relates to new compositions of matter classifiable in the field of organic chemistry as 2-hydrazino-2-thiazolines and the corresponding 2-azo-2-thiazoline derivatives thereof. More particularly, the instant invention relates to 2-phenylhydrazino-2-thiazolines and to the corresponding phenylazo derivatives thereof, which, optionally, may be further substituted in the ortho position of the phenyl ring and/or in the 1-position of hydrazino moiety; to methods of preparing these compounds; and to methods of employing them as anthelmintic agents, as antihypertensive agents and as ectoparasiticides.

In its composition aspect, therefore, the instant invention may be described as residing in the concept of 2-phenylhydrazino-2-thiazolines and the corresponding phenylazo derivatives thereof having the formula:

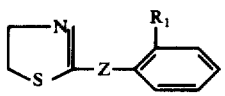

wherein $R_1$ is a member selected from the group consisting of hydrogen, loweralkyl and loweralkoxy, and Z is a member selected from the group consisting of:

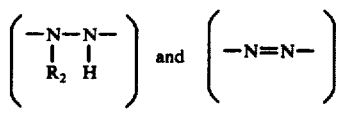

wherein $R_2$ is a member selected from the group consisting of hydrogen, loweralkanoyl, phenylacetyl, benzoyl, loweralkoxycarbonyl, phenoxycarbonyl, loweralkylsulfonyl, and phenylsulfonyl and the non-toxic pharmaceutically and agriculturally acceptable acid addition salts thereof.

As used above, the terms loweralkyl and loweralkoxy are intended to include both straight and branched chain alkyl and alkoxy groups having from 1 to 6 carbon atoms in the alkyl moiety such as, for example; methyl, ethyl, methoxy, propyl, isopropoxy, n-butoxy, isobutyl, n-hexyl, 2,3-dimethylbutoxy, and the like. The term loweralkanoyl includes both straight and branched chain alkanoyl groups having from 1 to 6 carbon atoms such as, for example; formyl, acetyl, propionyl, butyryl, isobutyryl, valeryl, isovalyryl, caproyl, and the like. The terms loweralkoxycarbonyl and loweralkylsulfonyl will include loweralkoxy carbonyl and loweralkylsulfonyl groups wherein the loweralkoxy and loweralkyl groups are as defined above. Pharmaceutically and agriculturally acceptable acid addition salts will include salts derived from mineral acids such as, for example; hydrochloric acid, hydrobromic acid, sulfuric acid, nitric acid, phosphoric acid and the like, and salts derived from aliphatic acids such as, for example; acetic acid, trimethylacetic acid, t-butylacetic acid and, propionic acid or salts derived from polycarboxylic acids such as, for example; citric acid, oxalic acid, lactic acid, succinic acid, and the like.

The instant invention is based upon applicants' discovery that the active thiazolines of this invention display inherent applied use characteristics as anthelmintic agents, as antihypertensive agents and as ectoparasiticides. The physiological activity of these thiazolines has been confirmed by standard laboratory techniques. It is contemplated, therefore, that pharmaceutical and agricultural formulations containing the thiazolines of this invention as the essential active ingredient will be employed in the treatment and control of helminthiasis hypertension and ectoparasites.

The 2-(phenylhydrazino)-2-thiazolines of this invention wherein $R_2$ in Formula I above is hydrogen readily may be prepared by employing as the starting material an appropriate ortho-$R_1$-phenylhydrazine conveniently, though not necessarily, in the form of its hydrohalide salt (i.e. hydrochloride, hydrobromide or hydroiodide). These ortho-$R_1$-phenylhydrazines are well-known compounds and are either available commercially or can be prepared by techniques already fully described in the chemical literature.

The ortho-$R_1$-phenylhydrazine starting material, in a suitable solvent such as, for example; methanol, ethanol, 2-propanol, dimethylformamide, dioxane, dimethoxyethane, tetrahydrofuran, acetonitrile or mixtures of these, either alone or with water, is treated with ammonium thiocyanate, desirably at reflux, for about 12 to about 36 hours. The reaction mixture than may be concentrated by distillation of the solvent and the solid residue washed with water and separated by filtration. Recrystallization from a suitable organic solvent such as, for example, methanol, ethanol, isopropanol, benzene, acetonitrile, dioxane, hexane, or the like yields the purified intermediate, 1-(ortho-$R_1$-phenyl)-3-thiosemicarbazide.

The 1-(ortho-$R_1$-phenyl)-3-thiosemicarbazide so produced then may be treated with a 2-haloethylamine (i.e. 2-chloroethylamine, 2-bromoethylamine, or 2-iodoethylamine), preferably in the form of its hydrohalide salt, in order to obtain the desired 2-(ortho-$R_1$-phenylhydrazino)-2-thiazoline end product. The reaction may be carried out by combining the thiosemicarbazide and the haloethylamine in a suitable organic solvent such as mentioned above and heating the mixture, usually at reflux, for about 8 to about 24 hours. The reaction mixture then is cooled to room temperature and filtered to separate the solid precipitate. The precipitate is dissolved in hot water, treated with aqueous alkali such as alkali metal bicarbonate or hydroxide, and the resulting precipitate is separated by filtration. Recrystallization of the precipitate by conventional techniques yields the desired 2-(ortho-$R_1$-phenylhydrazino)-2-thiazoline. This product, in addition to its physiological activity as disclosed above, also serves as a useful intermediate in the preparation of the other active thiazolines of this invention.

Typical 2-(ortho-$R_1$-phenylhydrazino)-2-thiazolines which may be prepared by the techniques described above will include, for example:

| Starting Material | End Product |
|---|---|
| phenylhydrazine | 2-(phenylhydrazino)-2-thiazoline |
| o-tolylhydrazine | 2-(o-tolylhydrazino)-2-thiazoline |
| o-methoxyphenylhydrazine | 2-(o-methoxyphenylhydrazino)-2-thiazoline |
| o-propylphenylhydrazine | 2-(o-propylphenylhydrazino)-2-thiazoline |

| Starting Material | End Product |
| --- | --- |
| o-butoxyphenylhydrazine | 2-(o-butoxyphenylhydrazino)-2-thiazoline |
| o-hexylphenylhydrazine | 2-(o-hexylphenylhydrazino)-2-thiazoline |

Any of the 2-(o-$R_1$-phenylhydrazino)-2-thiazolines prepared by the techniques described above are readily converted into the corresponding 2-(o-$R_1$-phenylazo)-2-thiazolines of Formula I by treating the hydrazino compound with a mild oxidizing agent. Useful oxidizing agents will include metal oxides such as, for example; silver oxide, mercuric oxide, and selenium dioxide; air, potassium ferricyanide, lead tetracetate, mercuric acetate, and peracids such as metachloroperbenzoic, peracetic, perbenzoic and the like. The reaction conveniently is carried out by treating the hydrazino starting material with the oxidizing agent in a suitable solvent such as ethyl acetate, benzene, dichloromethane, chloroform, ether, hexane, and the like at room temperature for about 12 to about 24 hours. The reaction mixture then is filtered and the filtrate is concentrated under reduced pressure. The residue then may be purified by conventional crystallization techniques to yield the desired 2-(ortho-$R_2$-phenylazo)-2-thiazoline.

Typical 2-(ortho-R1-phenylazo)-2-thiazolines prepared by the techniques described above will include, for example:

| Starting Material | End Product |
| --- | --- |
| 2-(phenylhydrazino)-2-thiazoline | 2-(phenylazo)-2-thiazoline |
| 2-(o-tolyhydrazino)-2-thiazoline | 2-(o-tolyazo)-2-thiazoline |
| 2-(o-ethoxyphenylhydrazino)-2-thiazoline | 2-(o-ethoxyphenylazo)-2-thiazoline |
| 2-(o-isopropylphenylhydrazino)-2-thiazoline | 2-(o-isopropoxyphenylazo)-2-thiazoline |
| 2-(o-pentylphenylhydrazino)-2-thiazoline | 2-(o-pentylphenylazo-2-thiazoline |
| 2-(o-hexyloxyphenylhydrazino)-2-thiazoline | 2-(o-hexyloxyphenylazo)-2-thiazoline |

The 2-(ortho-$R_1$-phenylhydrazino)-2-thiazolines also are readily converted into the 2-(2-$R_2$-1-ortho-$R_1$-phenylhydrazino)-2-thiazolines of Formula I ($R_2$ being other than hydrogen) by acylation. In general, the reaction may be carried out by treating the 2-(ortho-$R_1$-phenylhydrazino)-2-thiazoline with the desired acylating agent at room temperature up to reflux temperature. The reaction usually requires about 12 to 24 hours for completion. If desired, the reaction may be carried out in the presence of a suitable solvent such as, for example, pyridine, acetone, dimethylformamide, ethyl acetate and the like. After completion of the reaction, excess acylating agent (and solvent, if used) may be removed by distillation and the reaction mixture diluted with water and neutralized with aqueous alkali. The desired 2-(2-$R_2$-1-o-$R_1$-phenylhydrazino)-2-thiazoline then may be separated by filtration and purified by conventional recrystallization techniques.

In general, the preferred acylating agents used in the preparation of the 2-(2-$R_2$-1-o-$R_1$-phenylhydrazino)-2-thiazolines as described above are the corresponding acid halides (i.e. chloride, bromides, and iodides). Thus, loweralkanoyl halides, phenacetyl halides, benzoyl halides, loweralkoxycarbonyl halides, phenoxycarbonyl halides, loweralkylsulfonyl halides, and phenylsulfonyl halides usually will be employed in the acylation. The corresponding free acid or acid anhydride also may be employed if desired.

The novel compounds of this invention are active in the prevention and treatment of helminthiasis in the treatment of hypertension, and in the control of ectoparasites.

Helminthiasis is a widely occurring disease affecting animals, including man, and causes large economic losses in the domesticated animal industry. Particularly susceptible to the disease are ruminants such as sheep, cattle, and goats; and equines such as horses and mules. A wide variety of anthelmintic agents have been discovered and have varying degrees of efficacy on the particular helminths causing the infections. In view of the large economic interest in the prevention and control of helminthiasis, modern day research, in addition to seeking new classes of anthelmintically active materials, is also directed to finding ways for eliminating disadvantages in and improving the efficacy of the currently known anthelmintic agents.

While all of the thiazolines of this invention display anthelmintic activity as disclosed above, it will be obvious, of course, that these compounds will display varying degrees of potency depending upon the nature of the particular application contemplated and of the infectation to be combatted.

When the thiazolines of this invention are employed for the treatment and control of helminthiasis, the specific means employed for administering the thiazoline to the animal is not critical and any of the methods now used or available for treating animals infected with, or susceptible to infection by helminths are satisfactory. Where it is desired to administer the thiazoline in dry, solid unit dosage form, capsules, boluses or tablets containing the desired amount of thiazoline usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like.

Such unit dosage formulations may be varied widely with respect to their total weight and content of anthelmintic agent depending upon factors such as the type of host animal to be treated, the severity and type of infection and the weight of the host. For large animals such as sheep, swine, and cattle, unit dosages up to 15 gm., containing from 3 to 12 gm. of the thiazoline, may be employed. It is usually preferred, however, to employ unit dosages weighing from 5 to 10 gm. containing from 2 to 3 gm. of the thiazoline. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted thiazolines of this invention are mixed with a suspending agent such as bentonite and the solid mix is added to water just prior to administration. Alternatively, ready to use drench formulations, such as those described in U.S. Pat. No. 2,918,403; may be employed. Preferred drench formulations contain from about 5 to 50% by weight of the thiazoline.

The thiazolines described herein also may be administered as a component of the feed of the animals or may be dissolved or suspended in the drinking water. Such compositions comprise the thiazoline intimately dispersed in an inert carrier or diluent. By inert carrier is meant one that will not react with the thiazoline and one that may be administered safely to animals. Preferably, the carrier is one that is, or may be, an ingredient of the animal ration.

Suitable compositions include feed supplements in which the active ingredient is present in relatively large amounts and which are suitable for addition to the feed either directly or after an intermediate dilution or blending step. Typically carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active thiazolines are intimately dispersed throughout the carrier by methods such as grinding, stirring, milling or tumbling. Compositions containing from about 5 to 50% by weight of the thiazoline are particularly suitable as feed additives.

Examples of typical feed supplements containing the thiazolines of this invention dispersed in a solid carrier are:

|     |                                                            | lbs. |
| --- | ---------------------------------------------------------- | ---- |
| (A) | 2-(o-Tolylhydrazino)-2-thiazoline                          | 20   |
|     | Corn distiller's dried grains                              | 80   |
| (B) | 2-(o-Tolylazo)-2-thiazoline                                | 5    |
|     | Wheat Standard Middling                                    | 95   |
| (C) | 2-(2-Phenylacetyl-1-phenylhydrazino)-2-thiazoline          | 35   |
|     | Wheat shorts                                               | 65   |
| (D) | 2-[2-Ethoxycarbonyl-1-(o-ethoxyphenyl-hydrazino)]-2-thiazoline | 50 |
|     | Corn distiller's grains                                    | 50   |

These are similar feed supplements are prepared by uniformly mixing the thiazolines with the carrier.

Such supplements are added to the animal feed in an amount to give the finished feed the concentration of the thiazoline desired for the treatment and control of helminthiasis. Although the desired concentration of the active ingredient will vary depending upon the factors previously mentioned as well as upon the particular thiazoline employed. The thiazolines of this invention are usually fed at concentrations of between 0.5 to 2.0% in the feed in order to achieve the desired anthelmintic result.

Hypertension is a disorder in which the arterioles exhibit abnormal resistance to the flow of blood, usually associated with an abnormal increase in systolic, diastolic and mean arterial pressures, and symptomatically evidenced by fatigue, nervousness, dizziness, palpitation, insomnia, weakness, and headaches at some time in the course of the disorder. Angina pectoris and myocardial infarction due to coronary artery disease are frequent complications, while congestive failure may occur as a result of coronary insufficiency, or cardiac hypertrophy, or both factors in combination. It is a serious disease. For example, in humans, average life expectancy probably is close to twenty years from onset, with extremes of several years or several decades.

Etiologically, the cause of hypertension is not known and consequently, its therapy is uncertain. There is no treatment now known that consistently and completely reverses the cause of hypertension. Many symptoms of uncomplicated hypertension respond to the combination of reassurance by the doctor and time, but in most instances medicinal administration must be undertaken.

The selected compound may be administered either orally or by injection and the pharmaceutical preparations to accomplish this constitute a feature of this invention. For oral administration, the compound may simply be placed in gelatin capsules so that one or two of them will carry a unitary dosage into the patient. Or, tablets may be made up, using conventional tableting agents and procedures, so that one or two tablets will contain the amount of active compound to constitute a unitary dosage. In addition, the invention contemplates pharmaceutical preparations in the forms of elixirs and aqueous solutions and suspensions of such concentrations that the usual teaspoonful or two will serve as a unit dose.

The hypotensive agents of this invention find particular utility in the treatment of blood pressure abnormalities in animals, including man. The hypotensive compositions of this invention find agricultural use in the treatment of hypertensive disorders in domestic warmblooded vertebrates, for example in domestic fowl, such as turkeys, or mammals, such as domestic large animals, for example, in horses to control nosebleed, or to control capillary bleeding during surgery in cats, dogs, and other small animals.

The daily dose for humans is from 25 to 200 milligrams and this preferably is given to the patient in fractional amounts at intervals throughout the day. For example, a capsule would contain ten milligrams of the compound and one or two of them would be taken at a time, from one to four times a day. If larger daily doses are required, it would be preferably to put into a single capsule up to 200 mg. of the compound. This plan would be carried out with tablets although the smaller dosage single tablet could contain say 20 to 30 milligrams as the tablet can be scored to break it up into two or four pieces to be taken at a time. In like manner a conventional liquid pharmaceutical preparation may be prepared either for needle injection or oral consumption. The concentration per ml. or liquid ounce may be varied so that the doctor can adjust the dosage for the individual patient.

Dosages for veterinary administration vary, depending on the animal to be treated, but in general, fall in a range of about 0.1 to 10 mg/kg. per day. Formulations, as discussed above, are employed.

The instant compounds exhibit strong ectoparasiticidal activity in animals, including man, particularly against acarids which as animal ectoparasites infect domesticated animals, such as cattle, sheep and rabbits. At the same time, the active compounds which can be used according to the invention have only a slight toxicity to warm-blooded animals. They are therefore well suited for the control of animal ectoparasites.

As economically important ectoparasites of this Order, from the Family Ixodidae, which play a large part in tropical, subtropical and temperate latitutdes, there are mentioned for example:

The Australian and South American one-shot cattle tick *Boophilus microplus,* the Central and North American one-host cattle tick *Boophilus annulatus,* the African one-host cattle tick *Boophilus decoloratus.*

In addition, the instant compounds have activity against ticks of the genus Haemaphysalis particularly *Haemaphysalis longicornis,* also known as the 3 host cattle tick.

The ectoparasiticidal activity of the instant compounds is also noted against certain stages of fly parasites. In particular, the first instar larval stage of *Luciliia cuprina* or sheep blowfly.

In the course of time, ticks in particular have become resistant to the phosphoric acid esters and carbamates used hitherto as control agents, so that the success of control in many areas is to a growing extent rendered doubtful. To safeguard an economic livestock hubandry in the infestation areas, there is an urgent need for agents with which all development stages, that is to say larvae, nymphs, and adults of resistant strains, for example of the genus Boophilus, can be controlled with certainty. Examples of strains which are largely resistant to the phosphoric acid ester agents existing hitherto are, for example, in Australia the Ridgeland strain and the Biarra strain of *Boophilus microplus*.

The active compounds according to the invention are equally effective against the normally sensitive and against the resistant strains, for example of Boophilus. In customary application to the host animal, they not only act directly lethally on all forms parasitizing the animal but also act strongly ovicidally on the adult form, so that the propagation cycle of the ticks is interrupted in the parasitic phase on the animal as well as in the non-parasitic phase. The depositing of eggs is largely prevented, the development and the hatching inhibited.

The active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide dispersible carrier vehicles, such as solutions, emulsions, suspensions, emulifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers, including inert organic solvents, such as aromatic hydrocarbons (e.g. benzene, toluene, xylene, etc.), halogenated, especially chlorinated, aromatic hydrocarbons (e.g. chlorobenzenes, such as o-dichlorobenzene, trichlorobenzene, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanol-amine, etc.), ethers, etheralcohols (e.g. glycol monomethyl ether, etc.), amides (e.g. dimethyl formamide, etc.), pyrrolidones (e.g. N-methyl-pyrrolidone-2), sulfoxides (e.g. dimethyl sulfoxide, etc.), ketones (e.g. acetone, etc.) and/or water; as well as inert dispersible finely divided solid carriers, such as ground natural minerals (e.g. kaolins, alumina, silica, chalk, i.e. calcium carbonate, talc, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surfaceactive agents, for this purpose: emulsifying agents, such as non-ionic and/or anionic and/or cationic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, quaternary ammonium salts of longer, e.g. $C_{6-20}$, alkyl radicals, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially hygiene control or disinfectant agents, such as other parasiticides, or acaricides, insecticides, fungicides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or animal, e.g. livestock, application generally contemplate those in which the active compound is present in an amount substantially between about 0.001–5%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001–95%, and preferably 0.01–95%, by weight of the mixture.

It will be appreciated that the application concentrations are produced in connection with the above noted formulations normally by dilution with water. Furthermore, such concentrations can, according to the application form, be varied within a fairly wide range and are generally substantially between about 10 to 50,000 p.p.m. (g./g.), preferably between about 100 to 10,000 p.p.m., i.e. 0.001–5%, preferably 0.01–1%, as aforesaid.

Advantageously, the aqueous solutions or emulsions of the instant active compounds possess a markedly good stability under practical conditions, so that, even after standing for long periods at a pH in the range of from 7–9, such compounds may remain effective, i.e. even for three months or longer.

In particular, the present invention contemplates methods of selectively killing, combating or controlling pests, e.g. parasites, i.e. animal acarid ectoparasites, which comprise applying to at least one of correspondingly (a) such animal acarid ectoparasites, and (b) the corresponding habitat, i.e. the locus to be protected, e.g. the animal or livestock, a correspondingly combative or toxic amount, i.e. animal acarid ectoparasiticidally effective amount of the particular active compound of the invention alone or together with a carrier vehicle as noted above. The instant formulations or compositions are applied in the usual manner, for instance by spraying, atomizing, scattering, dusting, watering, i.e. as a bath (dip), sprinkling, pouring, and the like.

It will be realized, of course, that the concentration of the particular active compound utilized in admixture with the carrier vehicle will depend upon the intended application. Therefore, in special cases it is possible to go above or below the aforementioned concentration ranges.

The following examples are presented in order that the invention may be more fully understood. They are not to be construed as limitative of the invention.

EXAMPLE 1

1-(o-Tolyl)-3-Thiosemicarbazide

A mixture of 15.9 g. (0.1 moles) of o-tolylhydrazine hydrochloride, 15.2 g. (0.2 moles) of ammonium thiocyanate, 300 ml. of ethanol and 30 ml. of water are heated at reflux temperature for 24 hours, the solvent is removed by distillation at atmospheric pressure, and sufficient water added to cause precipitation. The aqueous suspension is filtered and the solid residue recrystallized from aqueous ethanol affording 15 g. (85%) of 1-(o-tolyl)-3-thiosemicarbazide, m.p. 158°–160° C.

EXAMPLE 2

2-(o-Tolylhydrazino)-2-Thiazoline

A mixture of 27.2 g. (0.15 moles) of 1-(o-tolyl)-3-thiosemicarbazide, 31 g. (0.15 moles) of 2-bromoethylamine hydrobromide, and 800 ml. of isopropanol are heated at reflux temperature for 16 hours. The reaction mixture is cooled to room temperature and filtered. The solid material is washed with hot water and the aqueous solution is treated with saturated sodium bicarbonate solution. The solid material which separates is filtered, washed with water, and recrystallized with methanol affording 13 g. of 2-(o-tolylhydrazino)-2-thiazoline, m.p. 126°–127° C.

EXAMPLE 3

2-(o-Tolylazo)-2-Thiazoline

To a stirred solution of 8.0 g. 2-(o-tolylhydrazino)-2-thiazoline in 400 ml. of ethyl acetate is added 4.0 g. of silver oxide. The reaction mixture is stirred for 18 hours at room temperature and filtered. The filtrate is evaporated to dryness in vacuo and the residue recrystallized from aqueous ethanol affording 6.7 g. of 2-(o-tolylazo)-2-thiazoline, m.p. 79°–80° C.

EXAMPLE 4

2-(2-Formyl-1-Phenylhydrazino)-2-Thiazoline

A mixture of 1.93 g. (0.01 moles) of 2-phenylhydrazinothiazoline in 20 ml. of 88% formic acid is heated at reflux temperature for 16 hours. The excess formic acid is removed for distillation at atmospheric pressure. The residue is combined with water and neutralized with 2.5N sodium hydroxide. The aqueous mixture is filtered and the residue recrystallized from ethanol affording 1.5 g. (68%) of 2-(2-formyl-1-phenylhydrazino)-2-thiazoline, m.p. 140°–141° C.

EXAMPLE 5

2-[2-Acetyl-1-(o-tolylhydrazino)]-2-Thiazoline

621 G. (0.03 moles) of 2-(o-tolylhydrazino)-2-thiazoline is combined with 5 ml. of acetic anhydride and stirred at room temperature for 5 minutes. The solid material is collected by filtration, washed with cooled ethanol, and recrystallized from ethanol affording 390 g. (52%) of 2-[2-acetyl-1-(o-tolylhydrazino)]-2-thiazoline, m.p. 147°–148° C.

EXAMPLE 6

2-(2-Phenylacetyl-1-Phenylhydrazino)-2-Thiazoline

To a solution of 2.0 g. of 2-(phenylhydrazino)-2-thiazoline in 10 ml. of dry pyridine and 20 ml. of dry benzene is added dropwise 2 ml. of phenyl acetyl chloride. The resulting mixture is heated at 60°–70° C. for 30 minutes and poured into 200 ml. of water. The benzene layer is separated and the aqueous solution washed once with 20 ml. of benzene. The combined benzene solutions are washed with water and 5% sodium carbonate solution and dried with anhydrous magnesium sulfate. The benzene is evaporated to dryness and hexane is added to the residue and the resulting suspension is filtered. The solid material is washed with hexane and recrystallized from a mixture of ethyl acetate and hexane affording 2-(2-phenylacetyl-1-phenylhydrazino)-2-thiazoline, m.p. 121°–124° C.

EXAMPLE 7

2-[2-Benzoyl-1-(o-Tolylhydrazino)]-2-Thiazoline

A mixture of 50 ml. of pyridine, 10 g. of 2-(o-tolylhydrazino)-2-thiazoline and 10 ml. of benzoyl chloride is stirred for one hour at 15° C. and allowed to stand at room temperature for 4 hours. The reaction mixture is poured into water and the resulting aqueous suspension filtered. The solid material is recrystallized from aqueous ethanol affording 9.6 g. of 2-[2-benzoyl-1-(o-tolylhydrazino)]-2-thiazoline, m.p. 177°–178° C.

EXAMPLE 8

2-[2-Ethoxycarbonyl-1-(o-ethoxyphenylhydrazino)]-2-Thiazoline

2 Ml. of ethyl chloroformate is added to a solution of 5 g. of 2-(o-ethoxyphenylhydrazino)-2-thiazoline in 20 ml. of pyridine at 0° C. The resulting solution is stirred for 30 minutes at room temperature and poured into 100 ml. of ice water. The solid material which separates is filtered and recrystallized from acetonitrile affording 4.1 g. of 2-[2-ethoxycarbonyl-1-(o-ethoxyphenylhydrazino)]-2-thiazoline, m.p. 81°–83° C.

EXAMPLE 9

2-[2-Phenoxycarbonyl-1-(o-propylphenylhydrazino)]-2-Thiazoline

Following the procedure of Example 8 using 4.5 g. of 2-(o-propylphenylhydrazino)-2-thiazoline, 5 ml. of phenyl chloroformate, and 50 ml. of pyridine there is obtained a quantitative yield of 2-[2-phenoxycarbonyl-1-(o-propylphenylhydrazino)]-2-thiazoline which is recrystallized from ethanol and has a m.p. of 117°–119° C.

EXAMPLE 10

2-[2-Methanesulfonyl-1-(o-Methoxyphenylhydrazino)-2-Thiazoline

A solution of 2.2 g. of 2-(o-methoxyphenylhydrazino)-2-thiazoline and 1.9 g. triethylamine in 25 ml. of dry benzene is treated with 1 ml. of methanesulfonyl chloride. The solution is stirred at room temperature for 1 hour and the solvent removed by distillation in vacuo. Water is added to the residue and the solid material collected by filtration and recrystallized from aqueous ethanol affording 1.7 g. of 2-[2-methanesulfonyl-1-(o-methoxyphenylhydrazino)]-2-thiazoline, m.p. 98°–99° C.

EXAMPLE 11

2-[2-Benzenesulfonyl-1-(o-Hexylphenylhydrazino)]-2-Thiazoline

To a stirred solution of 5.5 g. of 2-(o-hexylphenylhydrazino)-2-thiazoline in 25 ml. of dry pyridine and treated dropwise at room temperature with 3 ml. of benzene sulfonyl chloride. The reaction mixture is stirred overnight at room temperature and the solvent removed by distillation under reduced pressure at 40° C. Water is added and the aqueous mixture extracted with ethyl acetate. The ethyl acetate extracts are washed with water, dried, and evaporated in vacuo affording 4.2 g. of 2-[2-benzenesulfonyl-1-(o-hexylphenylhydrazino)]-2-thiazoline, m.p. 145°–146° C. after recrystallization from benzene.

EXAMPLE 12

2-Phenylhydrazino-2-Thiazoline Hydrochloride

A solution of 19.3 g. of 2-phenylhydrazino-2-thiazoline in 200 ml. of dry ethyl ether and 50 ml. of methanol is saturated with dry hydrogen chloride gas at 0° C. and stored at 0°–5° C. for 4 days. The crystalline material is filtered and washed with ether affording 16.5 g. of 2-phenylhydrazino-2-thiazoline hydrochloride, m.p. 300° C.

EXAMPLE 13

2-(o-Tolylhydrazino)-2-Thiazoline Citrate

A solution of 19.2 g. of citric acid in 50 ml. of methanol is added dropwise to a solution of 10 g. of 2-(o-tolylhydrazino)-2-thiazoline in 25 ml. of acetone. The reaction mixture is filtered and the solid material recrystallized from methanol affording 4.9 g. of 2-(o-tolylhydrazino)-2-thiazoline citrate, m.p. 97°–98° C.

What is claimed is:

1. The compound which is 2-phenylazo-2-thiazoline.
2. The compound which is 2-(o-tolylazo)-2-thiazoline.
3. The compound which is 2-(2-acetyl-1-phenylhydrazino)-2-thiazoline.
4. The compound which is 2-[2-formyl-1-(o-tolyl)-hydrazino]-2-thiazoline.
5. The compound which is 2-[2-acetyl-1-(o-tolylhydrazino)]-2-thiazoline.
6. The compound which is 2-[2-ethoxycarbonyl-1-(o-ethoxyphenylhydrazino)]-2-thiazoline.
7. The compound which is 2-[2-methanesulfonyl-1-(o-methoxyphenylhydrazino)]-2-thiazoline.

* * * * *